(12) United States Patent
Biester et al.

(10) Patent No.: US 10,299,838 B2
(45) Date of Patent: May 28, 2019

(54) METHOD AND INSTRUMENTS FOR INTERBODY FUSION AND POSTERIOR FIXATION THROUGH A SINGLE INCISION

(71) Applicant: Medos International Sarl, Le Locle (CH)

(72) Inventors: Eric Biester, Providence, RI (US); Ralph Solitario, Pocasset, MA (US)

(73) Assignee: Medos International Sarl, Le Locle (CH)

( * ) Notice: Subject to any disclaimer, the term of this patent is extended or adjusted under 35 U.S.C. 154(b) by 80 days.

(21) Appl. No.: 15/421,195

(22) Filed: Jan. 31, 2017

(65) Prior Publication Data

US 2017/0224391 A1  Aug. 10, 2017

Related U.S. Application Data

(60) Provisional application No. 62/292,205, filed on Feb. 5, 2016.

(51) Int. Cl.
*A61B 17/70* (2006.01)
*A61F 2/46* (2006.01)
(Continued)

(52) U.S. Cl.
CPC ........ *A61B 17/7074* (2013.01); *A61B 17/025* (2013.01); *A61B 17/3423* (2013.01);
(Continued)

(58) Field of Classification Search
CPC .............. A61B 17/7074; A61B 17/025; A61B 17/3423; A61B 2017/0256;
(Continued)

(56) References Cited

U.S. PATENT DOCUMENTS 4,573,448 A  3/1986 Kambin
4,646,738 A  3/1987 Trott
(Continued)

FOREIGN PATENT DOCUMENTS

CN  102727309 B  11/2014
DE  94 15 039 U1  11/1994
(Continued)

OTHER PUBLICATIONS

International Search Report and Written Opinion for Application No. PCT/US2015/043554, dated Nov. 19, 2015 (8 pages).
(Continued)

*Primary Examiner* — Pedro Philogene
*Assistant Examiner* — David C Comstock
(74) *Attorney, Agent, or Firm* — Nutter McClennen & Fish LLP

(57) ABSTRACT

A method of providing access to an intervertebral disc has been developed that involves using the patient's bony pedicle as an anchoring spot for a pedicle screw that temporarily attaches to the access port. One key element of the method is an assembly comprising: a) a screw extension comprising a shaft having a distal end portion comprising a receiver adapted for receiving a screw and a proximal end portion comprising a pivoting feature, b) a port comprising: i) a tubular wall defining a central passageway, ii) a longitudinal slot in the wall defining opposed ends of the wall, iii) opposed flanges extending radially from each end of the wall, and iv) a mating feature disposed in each opposed flanges adapted to pivotally mate with the pivoting feature of the screw extension, wherein the mating feature of the tube pivotally mates with the pivoting feature of the screw extension.

37 Claims, 8 Drawing Sheets

(51) Int. Cl.
    *A61B 17/34* (2006.01)
    *A61B 17/02* (2006.01)
(52) U.S. Cl.
    CPC ..... *A61F 2/4611* (2013.01); *A61B 2017/0256* (2013.01); *A61B 2017/3488* (2013.01); *A61F 2002/4635* (2013.01)
(58) Field of Classification Search
    CPC ........... A61B 2017/3488; A61F 2/4611; A61F 2002/4635
    USPC .................. 600/227, 228; 606/279, 86 A
    See application file for complete search history.

(56) References Cited

U.S. PATENT DOCUMENTS

| | | | |
|---|---|---|---|
| 4,678,459 A | 7/1987 | Onik et al. | |
| 4,863,430 A | 9/1989 | Klyce et al. | |
| 4,888,146 A | 12/1989 | Dandeneau | |
| 5,080,662 A | 1/1992 | Paul | |
| 5,195,541 A | 3/1993 | Obenchain | |
| 5,285,795 A | 2/1994 | Ryan et al. | |
| 5,395,317 A | 3/1995 | Kambin | |
| 5,439,464 A | 8/1995 | Shapiro | |
| 5,529,580 A | 6/1996 | Kusunoki et al. | |
| 5,540,706 A | 7/1996 | Aust et al. | |
| 5,569,290 A | 10/1996 | McAfee | |
| 5,591,187 A | 1/1997 | Dekel | |
| 5,601,569 A | 2/1997 | Pisharodi | |
| 5,662,300 A | 9/1997 | Michelson | |
| 5,688,222 A | 11/1997 | Hluchy et al. | |
| 5,730,754 A | 3/1998 | Obenchain | |
| 5,733,242 A | 3/1998 | Rayburn et al. | |
| 5,735,792 A | 4/1998 | Vanden Hoek et al. | |
| 5,820,623 A | 10/1998 | Ng | |
| 5,885,300 A | 3/1999 | Tokuhashi et al. | |
| 5,894,369 A | 4/1999 | Akiba et al. | |
| 5,899,425 A | 5/1999 | Corey, Jr. et al. | |
| 5,902,231 A * | 5/1999 | Foley | A61B 17/02 600/102 |
| 5,944,658 A * | 8/1999 | Koros | A61B 17/0206 600/231 |
| 5,954,635 A | 9/1999 | Foley et al. | |
| 6,033,105 A | 3/2000 | Barker et al. | |
| 6,053,907 A | 4/2000 | Zirps | |
| 6,063,021 A | 5/2000 | Hossain et al. | |
| 6,110,182 A | 8/2000 | Mowlai-Ashtiani | |
| 6,200,322 B1 | 3/2001 | Branch et al. | |
| 6,234,961 B1 | 5/2001 | Gray | |
| 6,283,966 B1 | 9/2001 | Houfburg | |
| 6,286,179 B1 | 9/2001 | Byrne | |
| 6,296,644 B1 | 10/2001 | Saurat et al. | |
| 6,322,498 B1 | 11/2001 | Gravenstein et al. | |
| 6,354,992 B1 | 3/2002 | Kato | |
| 6,371,968 B1 | 4/2002 | Kogasaka et al. | |
| 6,383,191 B1 | 5/2002 | Zdeblick et al. | |
| 6,447,446 B1 | 9/2002 | Smith et al. | |
| 6,468,289 B1 | 10/2002 | Bonutti | |
| 6,558,407 B1 | 5/2003 | Ivanko et al. | |
| 6,575,899 B1 | 6/2003 | Foley et al. | |
| 6,579,281 B2 | 6/2003 | Palmer et al. | |
| 6,626,830 B1 | 9/2003 | Califiore et al. | |
| 6,648,915 B2 | 11/2003 | Sazy | |
| 6,676,597 B2 | 1/2004 | Guenst et al. | |
| 6,688,564 B2 | 2/2004 | Salvermoser et al. | |
| 6,758,809 B2 | 7/2004 | Briscoe et al. | |
| 6,808,505 B2 | 10/2004 | Kadan | |
| 6,887,198 B2 | 5/2005 | Phillips et al. | |
| 6,983,930 B1 | 1/2006 | La Mendola et al. | |
| 7,087,058 B2 | 8/2006 | Cragg | |
| 7,104,986 B2 | 9/2006 | Hovda et al. | |
| 7,137,949 B2 | 11/2006 | Scirica et al. | |
| 7,182,731 B2 | 2/2007 | Nguyen et al. | |
| 7,341,556 B2 | 3/2008 | Shalman | |
| 7,434,325 B2 | 10/2008 | Foley et al. | |
| 7,591,790 B2 | 9/2009 | Pflueger | |
| 7,594,888 B2 | 9/2009 | Raymond et al. | |
| 7,618,431 B2 | 11/2009 | Roehm, III et al. | |
| 7,636,596 B2 | 12/2009 | Solar | |
| 7,637,905 B2 | 12/2009 | Saadat et al. | |
| 7,641,659 B2 | 1/2010 | Emstad et al. | |
| 7,771,384 B2 | 8/2010 | Ravo | |
| 7,794,456 B2 | 9/2010 | Sharps et al. | |
| 7,811,303 B2 | 10/2010 | Fallin et al. | |
| 7,931,579 B2 | 4/2011 | Bertolero et al. | |
| 7,946,981 B1 | 5/2011 | Cubb | |
| 7,951,141 B2 | 5/2011 | Sharps et al. | |
| 7,959,564 B2 | 6/2011 | Ritland | |
| 7,988,623 B2 | 8/2011 | Pagliuca et al. | |
| 8,007,492 B2 | 8/2011 | DiPoto et al. | |
| 8,038,606 B2 | 10/2011 | Otawara | |
| 8,043,381 B2 | 10/2011 | Hestad et al. | |
| 8,062,218 B2 | 11/2011 | Sebastian et al. | |
| 8,092,464 B2 | 1/2012 | McKay | |
| 8,096,944 B2 | 1/2012 | Harrel | |
| 8,202,216 B2 | 6/2012 | Melkent et al. | |
| 8,236,006 B2 | 8/2012 | Hamada | |
| 8,333,690 B2 | 12/2012 | Ikeda | |
| 8,360,970 B2 | 1/2013 | Mangiardi | |
| 8,372,131 B2 | 2/2013 | Hestad et al. | |
| 8,382,048 B2 | 2/2013 | Nesper et al. | |
| 8,397,335 B2 | 3/2013 | Gordin et al. | |
| 8,435,174 B2 | 5/2013 | Cropper et al. | |
| 8,460,180 B1 | 6/2013 | Zarate et al. | |
| 8,460,186 B2 | 6/2013 | Ortiz et al. | |
| 8,460,310 B2 | 6/2013 | Stern | |
| 8,518,087 B2 | 8/2013 | Lopez et al. | |
| 8,535,220 B2 | 9/2013 | Mondschein | |
| 8,556,809 B2 | 10/2013 | Vijayanagar | |
| 8,585,726 B2 | 11/2013 | Yoon et al. | |
| 8,602,979 B2 | 12/2013 | Kitano | |
| 8,622,894 B2 | 1/2014 | Banik et al. | |
| 8,636,655 B1 | 1/2014 | Childs | |
| 8,690,764 B2 | 4/2014 | Clark et al. | |
| 8,696,560 B2 * | 4/2014 | Strauss | A61B 1/32 600/206 |
| 8,721,536 B2 | 5/2014 | Marino et al. | |
| 8,740,779 B2 | 6/2014 | Yoshida | |
| 8,784,421 B2 | 7/2014 | Carrison et al. | |
| 8,821,378 B2 | 9/2014 | Morgenstern Lopez et al. | |
| 8,834,507 B2 | 9/2014 | Mire et al. | |
| 8,845,734 B2 | 9/2014 | Weiman | |
| 8,852,242 B2 | 10/2014 | Morgenstern Lopez et al. | |
| 8,870,753 B2 | 10/2014 | Boulais et al. | |
| 8,870,756 B2 | 10/2014 | Maurice | |
| 8,876,712 B2 | 11/2014 | Yee et al. | |
| 8,894,573 B2 | 11/2014 | Loftus et al. | |
| 8,894,653 B2 | 11/2014 | Solsberg et al. | |
| 8,926,502 B2 | 1/2015 | Levy et al. | |
| 8,932,207 B2 | 1/2015 | Greenburg et al. | |
| 8,932,360 B2 | 1/2015 | Womble et al. | |
| 8,936,605 B2 | 1/2015 | Greenberg | |
| 8,974,381 B1 | 3/2015 | Lovell et al. | |
| 8,986,199 B2 | 3/2015 | Weisenburgh, II et al. | |
| 8,992,580 B2 | 3/2015 | Bar et al. | |
| 9,028,522 B1 | 5/2015 | Prado | |
| 9,050,146 B2 | 6/2015 | Woolley et al. | |
| 9,055,936 B2 | 6/2015 | Mire et al. | |
| 9,072,431 B2 | 7/2015 | Adams et al. | |
| 9,078,562 B2 | 7/2015 | Poll et al. | |
| 9,131,948 B2 | 9/2015 | Fang et al. | |
| 9,144,374 B2 | 9/2015 | Maurice, Jr. | |
| 9,198,674 B2 | 12/2015 | Benson et al. | |
| 9,211,059 B2 | 12/2015 | Drach et al. | |
| 9,216,016 B2 | 12/2015 | Fiechter et al. | |
| 9,216,125 B2 | 12/2015 | Sklar | |
| 9,232,935 B2 | 1/2016 | Brand et al. | |
| 9,247,997 B2 | 2/2016 | Stefanchik et al. | |
| 9,265,491 B2 | 2/2016 | Lins et al. | |
| 9,277,928 B2 | 3/2016 | Morgenstern Lopez | |
| 9,307,972 B2 | 4/2016 | Lovell et al. | |
| 9,320,419 B2 | 4/2016 | Kirma et al. | |
| RE46,007 E | 5/2016 | Banik et al. | |
| RE46,062 E | 7/2016 | James et al. | |

(56) References Cited

U.S. PATENT DOCUMENTS

| | | |
|---|---|---|
| 9,386,971 B1 | 7/2016 | Casey et al. |
| 9,387,009 B2 * | 7/2016 | Fatone .................. A61B 5/0492 |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 2002/0022762 A1 | 2/2002 | Beane et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2005/0085692 A1 | 4/2005 | Kiehn et al. |
| 2005/0090848 A1 | 4/2005 | Adams |
| 2005/0143737 A1 * | 6/2005 | Pafford .............. A61B 17/7007 606/257 |
| 2005/0187570 A1 | 8/2005 | Nguyen et al. |
| 2005/0256525 A1 | 11/2005 | Culbert et al. |
| 2006/0206118 A1 | 9/2006 | Kim et al. |
| 2006/0211992 A1 | 9/2006 | Prosek |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0140120 A1 * | 6/2008 | Hestad .............. A61B 17/7085 606/246 |
| 2008/0188714 A1 | 8/2008 | McCaffrey |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0106261 A1 | 5/2011 | Chin et al. |
| 2011/0125158 A1 | 5/2011 | Diwan et al. |
| 2011/0130634 A1 * | 6/2011 | Solitario, Jr. ....... A61B 17/3421 600/231 |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0025121 A1 * | 1/2014 | Foley ................. A61B 17/1757 606/279 |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275793 A1 | 9/2014 | Song |
| 2014/0275799 A1 | 9/2014 | Schuele |
| 2014/0276840 A1 | 9/2014 | Richter et al. |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0287264 A1 | 10/2016 | Chegini et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2018/0098788 A1 * | 4/2018 | White ................ A61B 17/3423 |
| 2018/0153592 A1 * | 6/2018 | Larson ............... A61B 17/7074 |

FOREIGN PATENT DOCUMENTS

| | | |
|---|---|---|
| DE | 299 16 026 U1 | 11/1999 |
| EP | 0 537 116 A1 | 4/1993 |
| EP | 0 807 415 A2 | 11/1997 |

(56) References Cited

FOREIGN PATENT DOCUMENTS

| | | | |
|---|---|---|---|
| GB | 2481727 | A | 1/2012 |
| WO | 96/29014 | A1 | 9/1996 |
| WO | 01/56490 | A1 | 8/2001 |
| WO | 01/89371 | A1 | 11/2001 |
| WO | 02/02016 | A1 | 1/2002 |
| WO | 2004/103430 | A2 | 12/2004 |
| WO | 2008/121162 | A1 | 10/2008 |
| WO | 2009/033207 | A1 | 3/2009 |
| WO | 2013/033426 | A2 | 3/2013 |
| WO | 2013/059640 | A1 | 4/2013 |
| WO | 2014/050236 | A1 | 4/2014 |
| WO | 2014/100761 | A2 | 6/2014 |
| WO | 2014/185334 | A1 | 11/2014 |
| WO | 2016/111373 | A1 | 7/2016 |
| WO | 2016/131077 | A1 | 8/2016 |
| WO | 2016/168673 | A1 | 10/2016 |
| WO | 2017/006684 | A1 | 1/2017 |
| WO | 2017/015480 | A1 | 1/2017 |
| WO | 2017/083648 | A1 | 5/2017 |

OTHER PUBLICATIONS

International Search Report and Written Opinion for Application No. PCT/US2015/048485, dated Feb. 9, 2016. (16 pages).
International Search Report and Written Opinion for Application No. PCT/US2015/060978, dated Feb. 15, 2016 (8 pages).
Invitation to Pay Additional Fees for Application No. PCT/US2016/050022, dated Nov. 3, 2016 (2 pages).
International Search Report and Written Opinion for Application No. PCT/US2016/050022, dated Feb. 1, 2017 (19 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.
International Search Report and Written Opinion for Application No. PCT/US2017/016122, dated Sep. 7, 2017 (19 pages).

* cited by examiner

FIG. 12
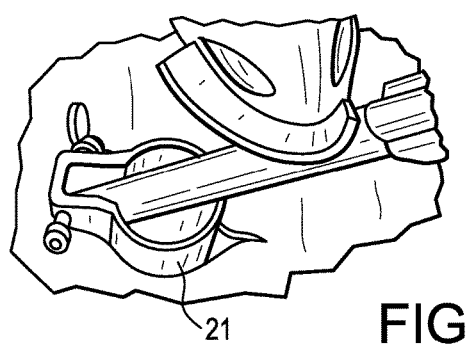
FIG. 13
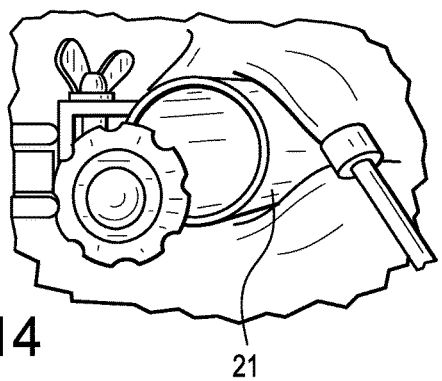
FIG. 14
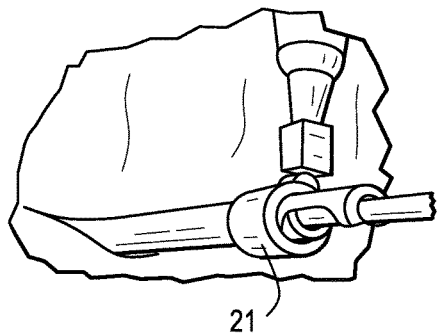
FIG. 15
FIG. 16
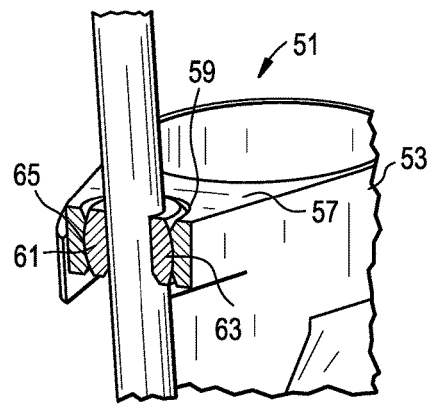
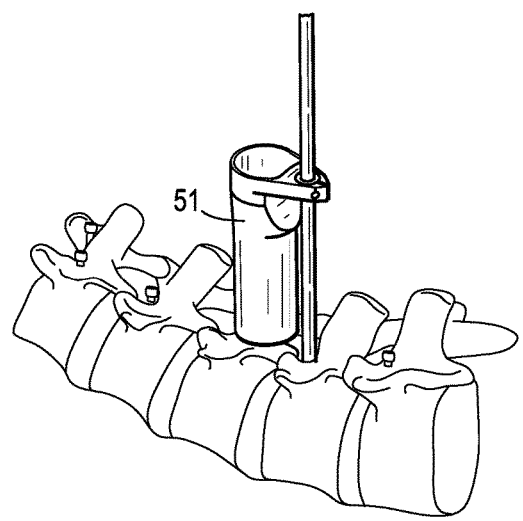

METHOD AND INSTRUMENTS FOR INTERBODY FUSION AND POSTERIOR FIXATION THROUGH A SINGLE INCISION

CONTINUING DATA

This application claims priority from U.S. Ser. No. 62/292,205, entitled "METHOD AND INSTRUMENTS FOR INTERBODY FUSION AND POSTERIOR FIXATION THROUGH A SINGLE INCISION", filed Feb. 5, 2016, the specification which is incorporated in its entirety.

BACKGROUND OF THE INVENTION

Articulating and expandable interbody fusion devices (IBDs) make it possible to perform interbody fusion procedures through a relatively small unilateral skin-and-facia incision compared to non-articulating or non-expandable IBDs. However, interbody fusion procedures are often supplemented with bilateral posterior fixation via pedicle screw-and-rod constructs whose large sizes require alteration of the IBD surgical access plan to accommodate posterior construct placement. The large size of the pedicle screw construct, when paired with interbody fusion, typically requires either lengthening of the incision used for IBD placement (mini-open) or additional incisions (percutaneous) through which the pedicle screws and rods are placed. These alterations may inhibit articulating and expandable IBD technology from realizing their full potentials as minimally invasive interbody fusion solutions. Therefore, a need exists for a means of achieving interbody fusion and posterior fixation through a single incision.

In addition, when minimally invasive spinal surgery procedures are used, the procedures typically include inserting a port through the initial incision and then passing the relevant tools and implants through the port on their way to the spine. Typically, the port is anchored to surgical table with large and bulky assembly components, thereby causing obstruction of the surgeon's view and workspace. Table mounts also have to be adjusted by a non-sterile member of the operating team, which takes control from the surgeon.

US 2011-0130634 (Solitario) discloses a patient-mounted retraction system.

SUMMARY OF THE INVENTION

A method of providing access to an intervertebral disc has been developed that involves using the patient's bony pedicle as an anchoring spot for an anchor (such as a pedicle screw) that temporarily attaches to the access port via an anchor extension (such as a screw extension). Because this new procedure eliminates the need for the surgical table as an anchor, it also eliminates the assembly components extending from the table to the port at the access site, thereby freeing the surgeon's view and workspace from bulky instruments while providing minimally invasive access. Preferably, the anchor extension is pivotally attached to the proximal end of the port so that it can pivot towards the center of the port and thereby provides access to two vertically-adjacent pedicles and to the intervertebral space therebetween.

Therefore, in accordance with the present invention, there is provided an assembly comprising:
a) an anchor extension comprising a shaft having a distal end portion comprising a receiver adapted for receiving an anchor and a proximal end portion comprising a pivoting feature,
b) a port comprising:
  i) a tubular wall defining a central passageway,
  ii) a longitudinal slot in the wall defining opposed ends of the wall,
  iii) opposed flanges extending radially from each end of the wall, and
  iv) a mating feature disposed in each opposed flanges adapted to pivotally mate with the pivoting feature of the screw extension.
    wherein the mating feature of the tube pivotally mates with the pivoting feature of the anchor extension.

Also in accordance with the present invention, there is provided a method of mounting a port to a patient having spinal surgery, comprising:
  a) passing a dilator through an incision in the skin of the patient towards a pedicle,
  b) passing a port having a passageway over the dilator, wherein the port comprises a tubular wall defining a central passageway,
  c) removing the dilator,
  d) passing an anchor assembly comprising a distal anchor and a proximal extension at least partially through the incision,
  e) inserting the distal anchor into the pedicle,
  f) pivotally attaching the proximal extension to the port.

Also in accordance with the present invention, there is provided a spinal assembly comprising:
a) an anchor extension comprising a shaft having a distal end portion comprising a receiver adapted for receiving an anchor and a proximal end portion comprising a pivoting feature,
b) an anchor received in the receiver of the screw extension,
c) a port comprising:
  i) a tube defining a first longitudinal passageway,
  ii) a flange extending radially from the tube and having a throughole longitudinally disposed therein,
  iii) a bushing having an inner perimeter and an outer perimeter, wherein the outer perimeter radially contacts the throughhole, and
wherein the anchor extension passes through the inner perimeter of the bushing.

Also in accordance with the present invention, there is provided an instrument assembly for performing MIS surgery on a spine, comprising:
  a) a port having a proximal end portion, a distal end portion, and an axial passageway defining a centerline, and
  b) an anchor extension having a distal end portion,
  wherein the anchor extension is pivotally attached to the proximal end portion of the port.

DESCRIPTION OF THE FIGURES

FIG. 12 discloses a step in which a rod is inserted through the dilator port, which is afforded by the slot in the dilator port.

FIG. 13 discloses a step in which set screws are placed through the dilator port and the screw/rod construct is tightened.

FIG. 14 discloses a step in which the dilator port is removed from the incision for subsequent closure.

FIG. 15 discloses an alternate embodiment of the assembly in which the port has a fully enclosed passageway and the screw extension is received in a bushing disposed in a flange extending from the port tube.

FIGS. 16-17 are alternate views of the assembly of FIG. 15 implanted in a patient's spine.

DETAILED DESCRIPTION OF THE INVENTION

Figure 1:
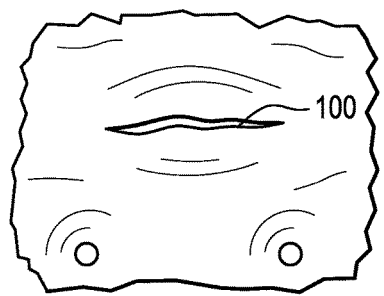
FIG. 1 discloses a first step of an embodiment wherein a paramedian skin and fascia incisions is made over the site through which interbody access is planned.
Figure 2:
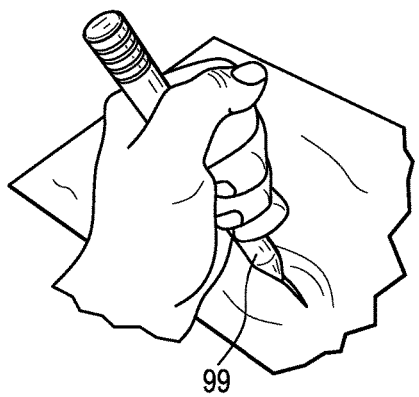
FIG. 2 discloses a second step wherein a conventional dilator is used to dilate and wand over the facet through which interbody access is planned.
Figure 3:
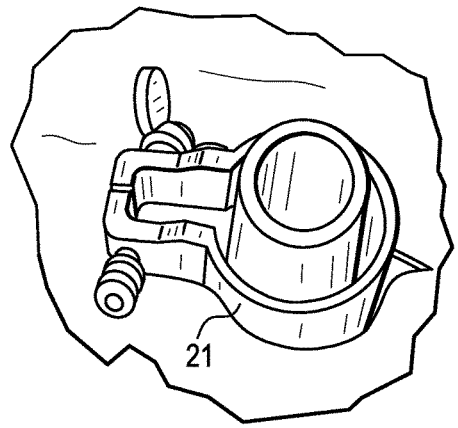
FIG. 3 discloses a third step in which an integrated tubular dilator port is placed over the standard dilator, and the inner dilator is removed.

Now referring to FIG. 1, a paramedian skin and fascia incision 100 is made over the site through which interbody access is planned. Now referring to FIG. 2, a conventional dilator 99 is used to dilate and wand over the facet through which interbody access is planned. Now referring to FIG. 3, an integrated tubular dilator port 21 is placed over the standard dilator, and the inner dilator is removed.

Figure 4:
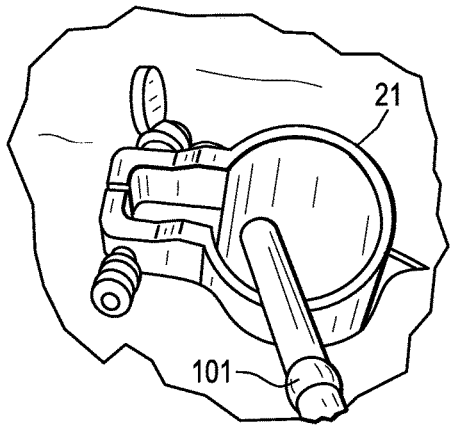
FIG. 4 discloses a step in which pedicle preparation is performed through the integrated dilator port for at least one pedicle screw.

FIG. 4 discloses a step in which pedicle preparation is performed through the integrated dilator port 21 for at least one pedicle screw. Thus, in some embodiments, the assembly further comprises a pedicle-preparation tool 101 at least partially disposed in the passageway. In some embodiments thereof, the tubular wall has a distal end, the pedicle-preparation tool has a working end, and the working end of the tool extends past the distal end of the tubular wall.

Figure 5A:
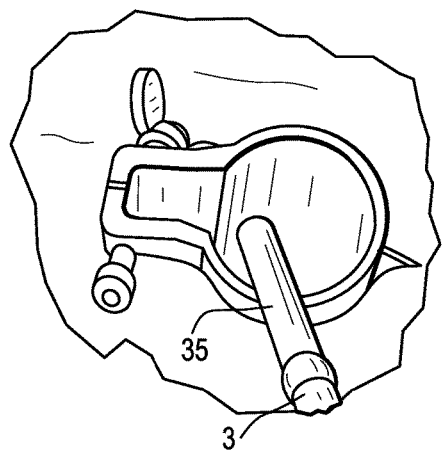
FIGS. 5A-B discloses a step in which a pedicle screw attached to a screw extension is inserted into one pedicle through the integrated dilator port, resulting in anchoring of the screw extension.
Figure 5B:
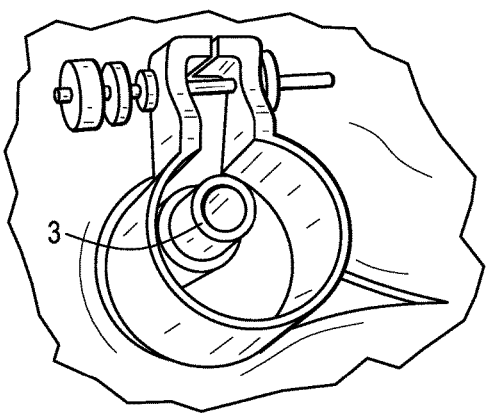

Now referring to FIGS. 5A and 5B, a pedicle screw 35 is attached to a screw extension 3 is inserted into one pedicle through the integrated dilator port.

Figure 6A:
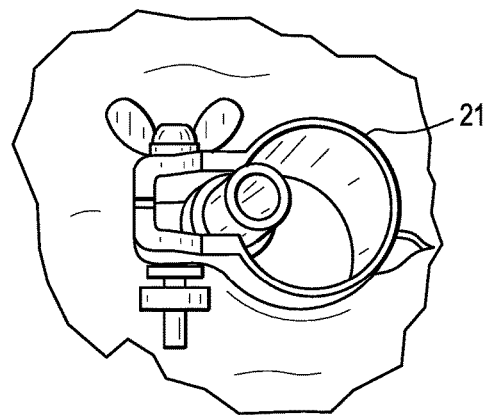
FIG. 6A discloses a step in which the integrated dilator port is proximally engaged with the screw extension via a spherical male feature on the extension and a proximally-located slotted cylindrical female feature on the dilator port. The dilator port height and angle are adjusted via the sphere-in-cylinder configuration, and the assembly is tightened via one of a variety of clamping mechanisms (such as a threaded clamping mechanism).

FIG. 6A discloses a step in which the integrated dilator port is proximally engaged with the screw extension via a spherical male feature on the extension and a proximally-located slotted cylindrical female feature on the dilator port. The dilator port height and angle are adjusted via the sphere-in-cylinder configuration, and the assembly is tightened via a threaded clamping mechanism.

Figure 6B:
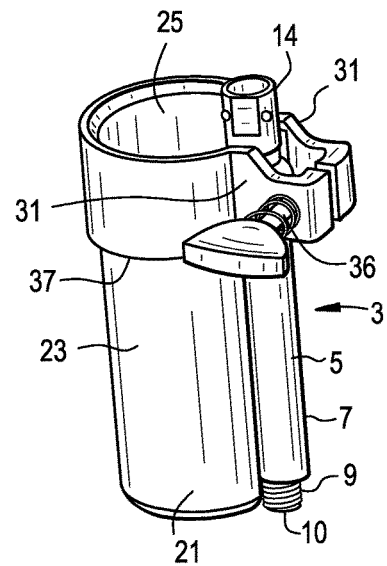
FIGS. 6B-D disclose different embodiments and views of the assembly.
Figure 6C:
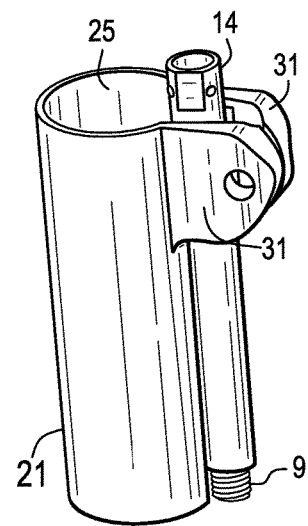
Figure 6D:
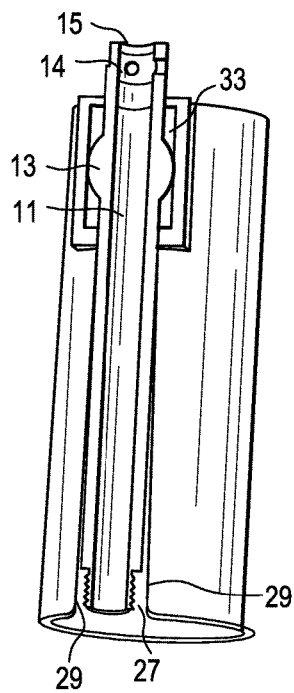

FIGS. 6B-D disclose an assembly 1 comprising:
a) a screw extension 3 comprising a shaft 5 having i) a distal portion 7 comprising a threaded receiver 9 located at the distal end portion 10 and adapted for receiving a screw and ii) a proximal portion 11 comprising a pivoting feature 13 and a head 14 located at the proximal end 15 of the screw extension,
b) a port 21 comprising:
  i) a tubular wall 23 defining a central passageway 25,
  ii) a longitudinal slot 27 in the wall defining opposed ends 29 of the wall,
  iii) opposed flanges 31 extending radially from each end of the wall, and
  iv) a mating feature 33 disposed in each opposed flanges adapted to pivotally mate with the pivoting feature of the screw extension.

wherein the mating feature of the tube pivotally mates in a joint with the pivoting feature of the screw extension.

FIG. 6B also comprises a locking feature 36 that locks the axial position of the screw extension vis-à-vis the port.

In some embodiments, the pivoting feature comprises a substantially spherically-shaped portion or bulb 13 extending from the shaft, as shown in FIGS. 6B-D. The spherical nature of this pivoting feature allows polyaxial pivoting (or "wanding") about the joint. The ability to wand the screw extension (i.e., pivot the screw extension about the joint) allows the surgeon to reach a vertically-adjacent pedicle with the same screw extension, thereby allowing two screws to be placed through a single port location.

Also as seen in FIG. 6B, the port has a circumferential ridge 37, which allows for controlling the rigidity required for clamping. The ridge helps transmit the clamping load.

FIG. 6C discloses an assembly substantially similar to that of FIG. 6B, except that the port does not have a circumferential ridge, and the locking feature have been omitted for clarity.

FIG. 6D shows a cross-section of an assembly substantially similar to that of FIGS. 6B and C. The FIG. 6D cross-section shows the bulb 13 of the screw extension as pivotally contacting the hemicylindrically-shaped longitudinal depressions 33 of the port.

Figure 6E:
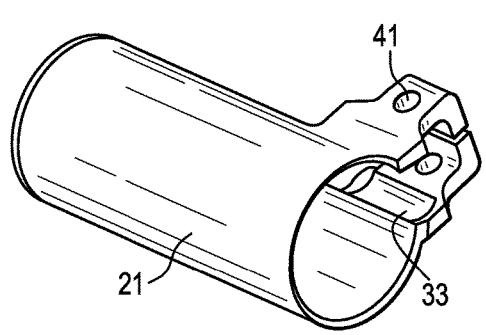
FIGS. 6E and 6F disclose alternate views of a port.
Figure 6F:
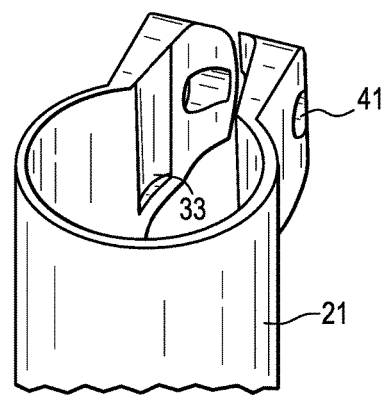

FIGS. 6E and 6F show alternate embodiments of the port component 21 disattached from the screw extension.

In FIGS. 6E and 6F, the mating features of the port flanges that allow mating with the screw extension are hemicylindrically-shaped longitudinal depressions 33 disposed in each of the opposed flanges adapted to pivotally mate with the pivoting feature of the screw extension. The hemicylindrical nature of the depressions allow the bulb 13 of the screw extension to slide in a proximal-distal (axial) direction, thereby facilitating initial attachment of the bulb to the port and allowing the surgeon freedom to choose the height of the joint in the assembly so as to reduce tissue creep distal to the port. Also in FIGS. 6E and 6F, the flanges have opposed holes 41 adapted to receive the pin of a locking feature (not shown).

In some embodiments, each mating feature comprises a depression. Preferably, the depression has a curve that allows the screw extension to pivot therein. In some embodiments, each mating feature comprises a substantially hemi-cylindrically-shaped depression extending in the proximal-distal direction that allows the screw extension to polyaxially pivot therein, thereby allowing wanding.

In some embodiments, each mating feature 33 comprises a substantially cylindrically-shaped depression having a longitudinal axis extending in a direction substantially parallel to the central passageway, as shown in FIGS. 6E and 6F. The shape of this depression not only allows the above-mentioned pivoting, it also allows axial movement of the pivoting feature of the screw extension in a direction parallel to the longitudinal axis of the passageway. This freedom of axial movement in the screw extension is important because it allows the surgeon to mate the distal end of the port with the bony anatomy to minimize soft tissue creep without having to adjust the screw depth.

Figure 6G:
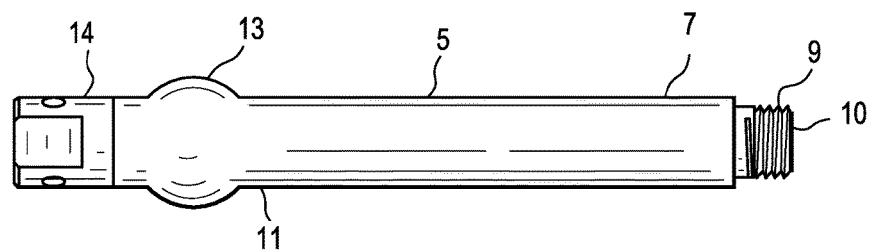
FIG. 6G-I disclose side and cross-sectional views of a screw extension having a bulb.
Figure 6H:
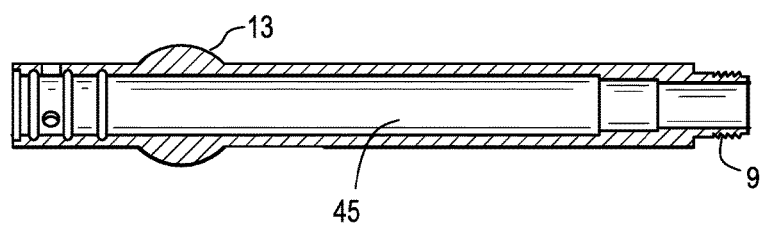
Figure 6I:
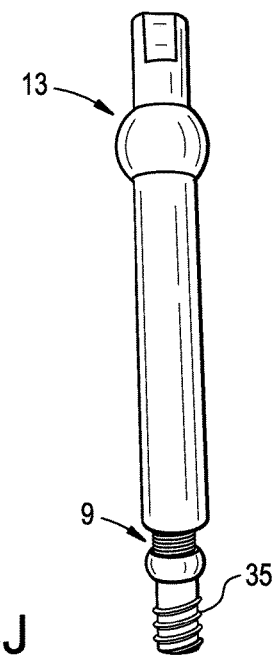

FIGS. 6G-6I disclose different views of a screw extension. In FIG. 6G, the shaft of the screw extension has a substantially spherically-shaped bulb extending therefrom. This bulb, which is located on the proximal portion of the screw extension, is the pivoting feature of the screw extension that pivots with the depressions of the flanges of the port. FIG. 6F also discloses a threaded receiver on the distal end portion of the extension that is adapted for attaching to a pedicle screw. FIG. 6H is a cross-section of FIG. 6G, which reveals a bore 45 adapted for passage of a pedicle screw. Proximal to the bulb of FIGS. 6G and 6H is a head located at the proximal end of the screw extension and adapted to attach to a screw driver. The head has a pair of diametrically aligned holes 47 adapted to retain the extension on the screw driver during insertion. FIG. 6I shows a screw extension having a spherical bulb pivoting feature 13, and distal threads 9.

In some embodiments, as in FIG. 6I, the assembly further comprises a screw 35 received in the receiver of the screw extension.

Figure 6J:
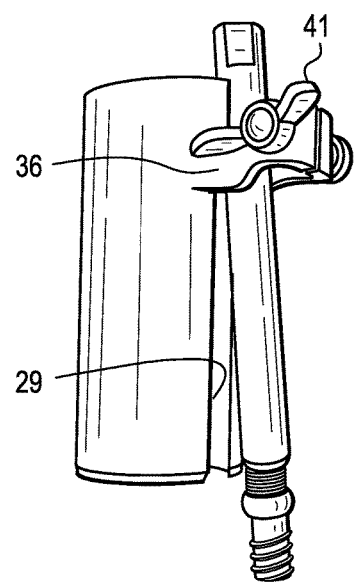
FIGS. 6J-K disclose the assembly further comprising a locking feature adapted to lock the screw extension between the flanges of the port.
Figure 6K:
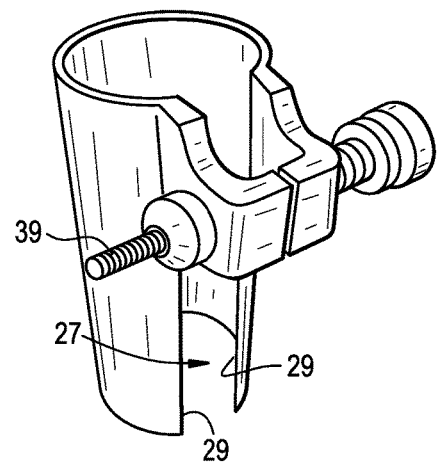

Now referring to FIGS. 6J-K, in preferred embodiments, the assembly further comprises a locking feature 36 adapted to lock the screw extension between the flanges of the port. This locking mechanism keeps the screw extension attached to the port with its axial position maintained while allowing the screw extension to pivot about the joint. In some embodiments, the locking feature is produced by providing opposed holes in the opposed flanges, inserting a threaded pin 39 through the opposed holes, and tightening a nut 41 over a distal end of the threaded pin. The resulting locking feature of is shown in FIG. 6B.

FIG. 6K further shows, in addition to the locking feature, the slot 27 defined in the port by the two ends 29 of its wall.

Figure 7:
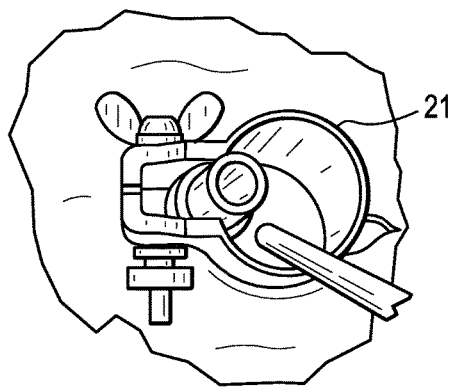
FIG. 7 discloses a step in which facetectomy and discectomy are performed and the IBD is placed through the integrated dilator port.

Now referring to FIG. 7, facetectomy and discectomy are performed and the IBD is placed through the integrated dilator port 21.

Figure 8:
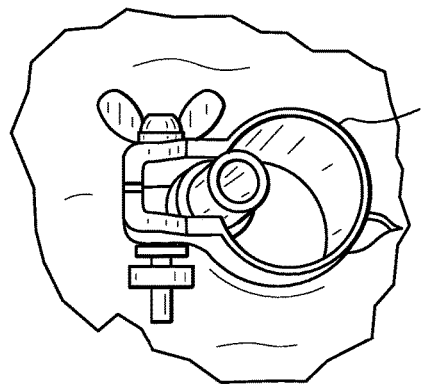
FIG. 8 discloses a step in which the angle and height of the dilator port are adjusted, for subsequent screw placement. Access to the adjacent screw trajectory is afforded by the slot in the dilator port that allows it to pass over the screw extension.

Now referring to FIG. 8, the angle and height of the dilator port are adjusted, for subsequent screw placement. Access to the adjacent screw trajectory is afforded by the slot in the dilator port that allows it to pass over the screw extension.

Figure 9:
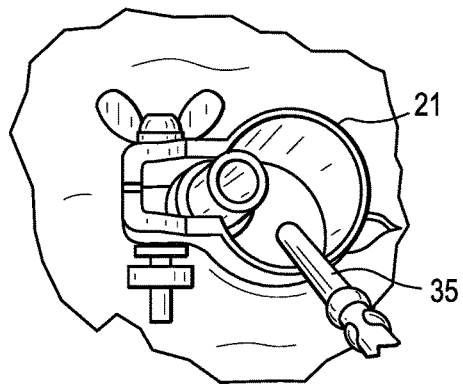
FIG. 9 discloses a step in which an adjacent level screw is placed through the dilator port, FIG. 10 discloses a step in which the dilator port is disengaged from the screw extension and the screw extension is removed from the screw.
Figure 10:
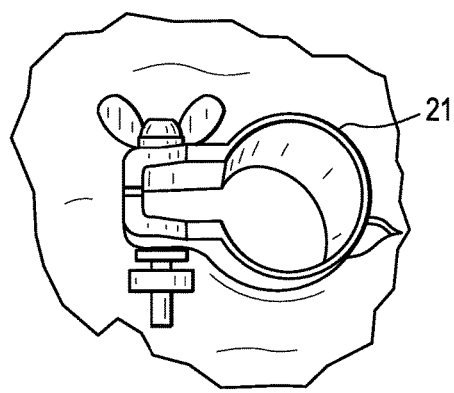

Now referring to FIG. 9, an adjacent level screw is placed through the dilator port, Now referring to FIG. 10, the dilator port is disengaged from the screw extension and the screw extension is removed from the screw.

Figure 11:
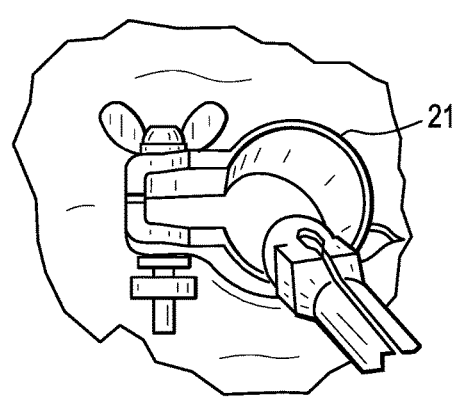
FIG. 11 discloses a step in which heads are assembled to the screw shanks through the dilator port.

Now referring to FIG. 11, heads are assembled to the screw shanks through the dilator port.

Now referring to FIG. 12, a rod is inserted through the dilator port, which is afforded by the slot in the dilator port.

Now referring to FIG. 13, set screws are placed through the dilator port and the screw/rod construct is tightened.

Now referring to FIG. 14, the dilator port is removed from the incision for subsequent closure. Although FIG. 14 shows final tightening as well, final tightening can occur before or after the port is removed.

Figure 17:
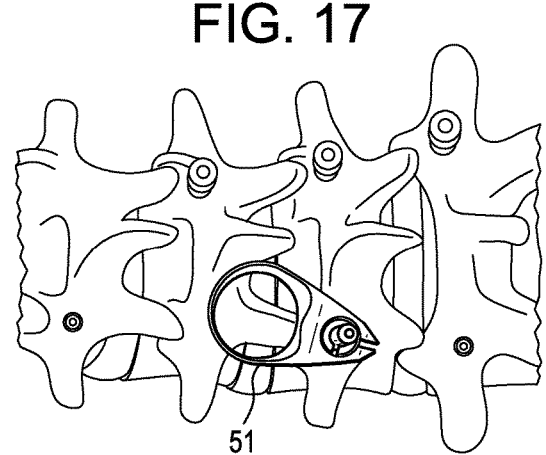

Referring now to FIG. 15-17, there is provided an assembly comprising:
a) a screw extension comprising a shaft having a distal end portion comprising a receiver adapted for receiving a screw and a proximal end portion comprising a pivoting feature,
b) a screw received in the receiver of the screw extension.
c) a port 51 comprising:
  j) a tube 53 defining a first longitudinal passageway 55,
  ii) a flange 57 extending radially from the tube and having a throughhole 59 longitudinally disposed therein,
  iii) a bushing 61 having an inner perimeter 63 and an outer perimeter 65, wherein the outer perimeter radially contacts the throughhole, and
wherein the screw extension passes through the inner perimeter of the bushing.

In alternate embodiments related to FIGS. 15-17, a vertical slot is provided in the port so as to fulfill the need of being able to perform the complete procedure through a single incision.

Preferably, the bushing is a split bushing intended to transmit a clamping load from the port housing to the screw extension to maintain both rotational and axial stability of the port relative to the screw extension. Preferably, the bushing is flexible to allow wanding of the screw extension. Also preferably, the bushing is located adjacent a proximal end of the tube, again to allow wanding of the screw extension. The ability to wand the screw extension (i.e., pivot the screw extension about the bushing) allows the surgeon to reach an adjacent pedicle with the screw extension, thereby enabling two screws to be placed through a single port location.

Figures 18A, 18B, 19A, 19B:
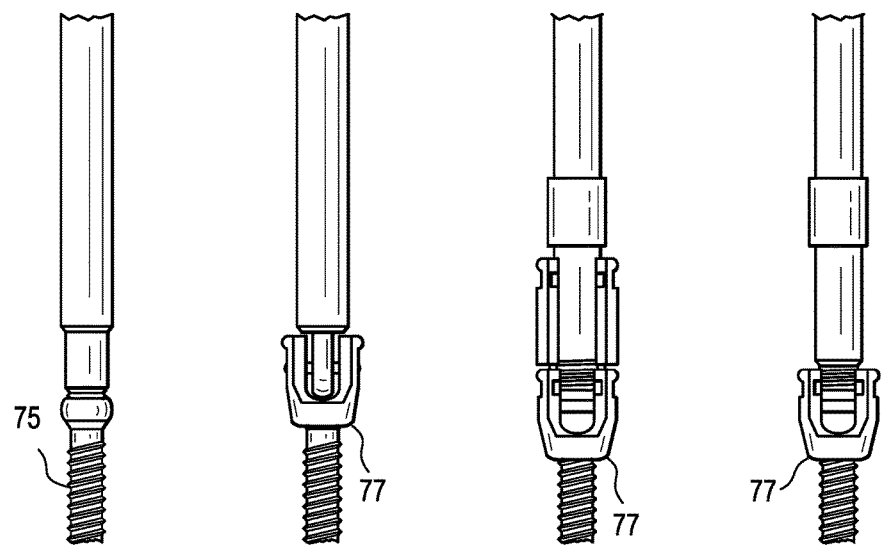
FIGS. 18A-B disclose the screw extension of the invention attached to a pedicle screw in a monoaxial or co-axial fashion.
FIGS. 19A-B disclose the screw extension of the invention attached to a pedicle screw in a polyxial (lockable) fashion.

The instruments associated with the proposed solution would likely be classified as general surgical instruments. The screw extension would interface with a pedicle screw system, such as the MATRIX or EXPEDIUM systems marketed by DePuy Synthes Spine (Raynham, Mass.). Similar to the MATRIX system distraction tips, the screw extension could interface with a headless screw shank 75 in a monoaxial fashion (as shown in FIGS. 18A-B) or with a polyaxial screw head 77 in a lockable polyaxial fashion (as shown in FIGS. 19A-B).

We claim:
1. An assembly comprising:
  a) an anchor extension comprising a shaft having a distal end portion comprising a receiver adapted for receiving an anchor and a proximal end portion comprising a pivoting feature;
  b) a port comprising:
    i) a tubular wall defining a central passageway,
    ii) a longitudinal slot in the wall defining opposed ends of the wall, iii) opposed flanges extending radially from each end of the wall, and iv) a mating feature disposed in each of the opposed flanges adapted to pivotally mate with the pivoting feature of the anchor extension, wherein the mating feature disposed in each flange pivotally mates with the pivoting feature of the anchor extension.

2. The assembly of claim 1 wherein each mating feature comprises a depression.

3. The assembly of claim 1 wherein each mating feature comprises a substantially spherically-shaped depression.

4. The assembly of claim 1 wherein each mating feature comprises a substantially cylindrically-shaped depression having a longitudinal axis extending in a direction substantially parallel to the central passageway.

5. The assembly of claim 1 wherein each mating feature comprises a hole.

6. The assembly of claim 1 wherein the pivoting feature comprises a substantially spherically-shaped portion extending from the shaft.

7. The assembly of claim 1 further comprising a locking feature adapted to lock the anchor extension between the flanges of the port.

8. The assembly of claim 1 wherein the flanges have opposed holes and the assembly further comprises:

c) a threaded pin inserted through the opposed holes.

9. The assembly of claim 8 further comprising:

d) a nut threadably attached to the threaded pin.

10. The assembly of claim 1 further comprising:

c) a screw received in the receiver of the anchor extension.

11. The assembly of claim 10 further comprising:

d) a pedicle-preparation tool at least partially disposed in the passageway.

12. The assembly of claim 11 wherein the tubular wall has a distal end, the pedicle-preparation tool has a working end, and the working end of the tool extends past the distal end of the tubular wall.

13. The assembly of claim 10 further comprising:

e) an implant at least partially disposed in the passageway.

14. The assembly of claim 1 wherein the anchor extension is a screw extension.

15. The assembly of claim 1, wherein the anchor extension is pivotally attached to a proximal end portion of the port.

16. The assembly of claim 1, wherein the distal end portion of the anchor extension can move substantially towards a centerline of the central passageway of the port during pivoting action.

17. The assembly of claim 1, wherein the anchor extension is adapted to pivot in a single plane.

18. The assembly of claim 1, wherein the anchor extension is adapted to pivot polyaxially.

19. The assembly of claim 1, wherein the anchor extension is provided in the slot.

20. The assembly of claim 1, wherein the pivotal mating occurs inside the passageway.

21. A method of mounting a port to a patient having spinal surgery, comprising:

a) passing a dilator through an incision in the skin of the patient towards a pedicle;

b) passing a port over the dilator, wherein the port comprises a tubular wall defining a central passageway;

c) removing the dilator;

d) passing an anchor assembly comprising a distal anchor and a proximal anchor extension at least partially through the central passageway of the tube;

e) inserting the distal anchor into the pedicle; and f) pivotally attaching the proximal extension to the port.

22. The method of claim 21 wherein the proximal extension is adapted to pivot towards a centerline of the passageway of the port.

23. The method of claim 21 wherein the anchor assembly at least partially passes through or outside the passageway of the port.

24. The method of claim 21 wherein the anchor is a screw.

25. The method of claim 21 further comprising:

g) passing a pedicle-preparation tool at least partially through the passageway.

26. The method of claim 25 further comprising:

h) inserting a second anchor through the passageway and into a second pedicle without detaching the port from the screw assembly.

27. The method of claim 26 further comprising:

i) inserting a rod through the passageway.

28. The method of claim 27 further comprising:

j) inserting a second anchor through the passageway and into the second pedicle without detaching the port from the screw assembly.

29. The method of claim 28 further comprising:

k) attaching the rod to the distal anchor and the second anchor.

30. A spinal assembly comprising:

a) an anchor extension comprising a shaft having a distal end portion comprising a receiver adapted for receiving an anchor and a proximal end portion comprising a pivoting feature;

b) an anchor received in the receiver of the anchor extension;

c) a port comprising:

i) a tube defining a first longitudinal passageway, ii) a flange extending radially from the tube and having a throughhole longitudinally disposed therein, iii) a bushing having an inner perimeter and an outer perimeter, wherein the outer perimeter radially contacts the throughhole, and wherein the anchor extension is pivotally attached to the tube by passing the distal end portion of the anchor extension through the inner perimeter of the bushing disposed within the throughhole of the flange such that the pivoting feature at the proximal end portion of the anchor extension pivotally mates with the bushing.

31. The assembly of claim 30 wherein the bushing is flexible to allow wanding of the anchor extension.

32. The assembly of claim 30 wherein the bushing is located adjacent a proximal end of the tube.

33. The assembly of claim 30, wherein the pivotal mating occurs outside the passageway.

34. The assembly of claim 30, having a tool disposed in the passageway.

35. The assembly of claim 30, having an implant disposed in the passageway.

36. The assembly of claim 30, wherein the anchor extension is a screw extension.

37. A method of mounting a port to a patient having spinal surgery, comprising:

a) passing a dilator through an incision in the skin of the patient towards a pedicle;

b) passing a port over the dilator, wherein the port comprises a tube defining a first longitudinal passageway, a flange extending radially from the tube and having a throughhole longitudinally disposed therein, and a bushing disposed within the throughhole of the flange, wherein the bushing has an inner perimeter and an outer perimeter and the outer perimeter radially contacts the throughhole;

c) removing the dilator;
d) passing an anchor assembly comprising a distal anchor and a proximal anchor extension at least partially through the inner perimeter of the bushing disposed within the throughhole of the flange;
e) inserting the distal anchor into the pedicle; and
f) pivotally mating a pivoting feature of the proximal anchor extension with the bushing.

* * * * *